(12) United States Patent
Hsieh

(10) Patent No.: US 6,490,333 B1
(45) Date of Patent: Dec. 3, 2002

(54) METHODS AND APPARATUS FOR CONE-TILTED PARALLEL SAMPLING AND RECONSTRUCTION

(75) Inventor: Jiang Hsieh, Brookfield, WI (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 10/034,135

(22) Filed: Dec. 28, 2001

(51) Int. Cl.⁷ .................................................. A61B 6/03

(52) U.S. Cl. ............................. 378/4; 378/19; 378/901

(58) Field of Search ........................... 378/4, 8, 15, 19, 378/901

(56) References Cited

U.S. PATENT DOCUMENTS

| 5,802,134 A | * | 9/1998 | Larson et al. .................. 378/15 |
| 5,881,122 A | * | 3/1999 | Crawford et al. .............. 378/15 |
| 5,887,047 A | * | 3/1999 | Bailey et al. ................... 378/4 |
| 5,909,477 A | * | 6/1999 | Crawford et al. .............. 378/4 |

* cited by examiner

Primary Examiner—David V. Bruce
(74) Attorney, Agent, or Firm—Carl B. Horton, Esq.; Armstrong Teasdale LLP

(57) ABSTRACT

A method for reconstructing a computed tomographic (CT) image of an object is provided. The method includes initializing a CT imaging system in a step-and-shoot mode, scanning an object to generate a plurality of adjacent axial scans, wherein the distance between the adjacent axial scans is approximately equal to a projected detector height at the detector iso-center, and reconstructing an image of the object using the adjacent axial scans.

29 Claims, 5 Drawing Sheets

METHODS AND APPARATUS FOR CONE-TILTED PARALLEL SAMPLING AND RECONSTRUCTION

BACKGROUND OF THE INVENTION

This invention relates to tomographic imaging, and more particularly to methods and apparatus for cone-tilted parallel sampling and reconstruction.

In at least one known CT imaging system configuration, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated beam radiation received at the detector array is dependent upon the attenuation of an x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

With the introduction of multi-slice CT imaging systems, research activities on multi-slice helical reconstruction have become the focus of many studies. Some known CT imaging systems address the issue of incomplete data sampling by using various approximation methods. These methods have been shown to be quite successful in producing clinically acceptable image quality even at fairly high helical pitches although little attention has been paid, however, in the area of reconstruction algorithms for the step-and-shoot (axial) mode CT imaging system.

For example, in some CT imaging systems, as the number of slices, and z coverage, increase, each projection view can cover a significant portion of an anatomical organ. As a result, the relative importance of the step-and-shoot or axial mode increases. For a 32-slice CT imaging system with a detector cell aperture of 0.625 mm, with a z-coverage of 20 mm, a cardiac scan can be completed in 6 axial scans. With a gantry speed of 0.5s per rotation, the entire heart can be covered in a single breath-hold. If a multi-sector reconstruction approach is utilized to improve temporal resolution and to freeze cardiac motion, the scan protocol is simpler as compared to the helical mode since the patient table moves to the next location only when sufficient data has been collected. In this approach, prospective gating of the x-ray with EKG signals can be easily achieved.

With the increased number of detector rows and increased z-coverage, cone beam artifact related issues become more important. For moderate cone angle, the Feldkamp (FDK) reconstruction algorithm has been shown to be sufficient. The FDK algorithm utilizes a three-dimensional backprojection to accurately backproject the filtered projections along the actual x-ray path, instead of the two-dimensional backprojection that approximates a ray path by a line that is parallel to the reconstructed image. Although the FDK algorithm has been shown to be sufficient for moderate cone angles, the FDK algorithm reduces the z-coverage of the scan.

BRIEF SUMMARY OF THE INVENTION

In one embodiment, a method for reconstructing a computed tomographic (CT) image of an object is provided. The method includes initializing a CT imaging system in a step-and-shoot mode, scanning an object to generate a plurality of adjacent axial scans, wherein the distance between the adjacent axial scans is approximately equal to a projected detector height at the detector iso-center, and reconstructing an image of the object using the adjacent axial scans.

In another embodiment, a method for reconstructing a computed tomographic (CT) image of an object is provided. The method includes initializing a CT imaging system in a step-and-shoot mode, performing at least one axial scan to generate a plurality of projection samples, rebinning the projection samples to a set of tilted parallel geometry samples, and reconstructing an image of the object using the rebinned projection samples.

In a further embodiment, a computed tomographic (CT) imaging system for reconstructing an image of an object is provided. The imaging system includes a detector array, at least one radiation source, and a computer coupled to the detector array and the radiation source. The computer is configured to initialize a CT imaging system in a step-and-shoot mode, scan an object to generate a plurality of adjacent axial scans, wherein the distance between the adjacent axial scans is approximately equal to a projected detector height at the detector iso-center, and reconstruct an image of the object using the adjacent axial scans.

In a still further embodiment, a computer readable medium encoded with a program executable by a computer for reconstructing an image of an object is provided. The program is configured to instruct the computer to initialize a CT imaging system in a step-and-shoot mode, scan an object to generate a plurality of adjacent axial scans, wherein the distance between the adjacent axial scans is approximately equal to a projected detector height at the detector iso-center, and reconstruct an image of the object using the adjacent axial scans.

DETAILED DESCRIPTION OF THE INVENTION

As used herein, an element or step recited in the singular and preceded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 1:
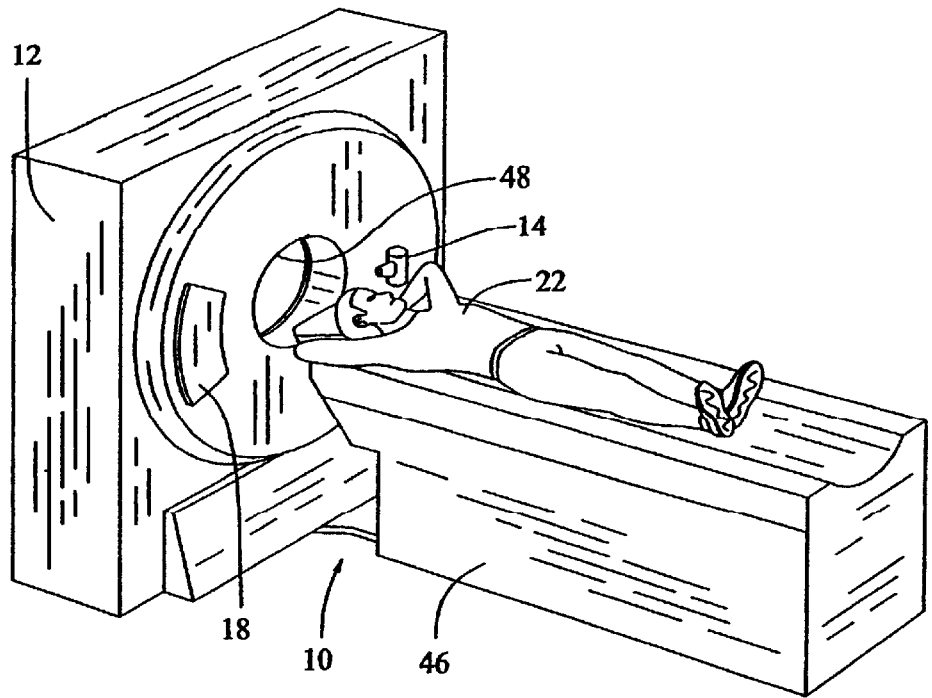
FIG. 1 is a pictorial view of a CT imaging system.
Figure 2:
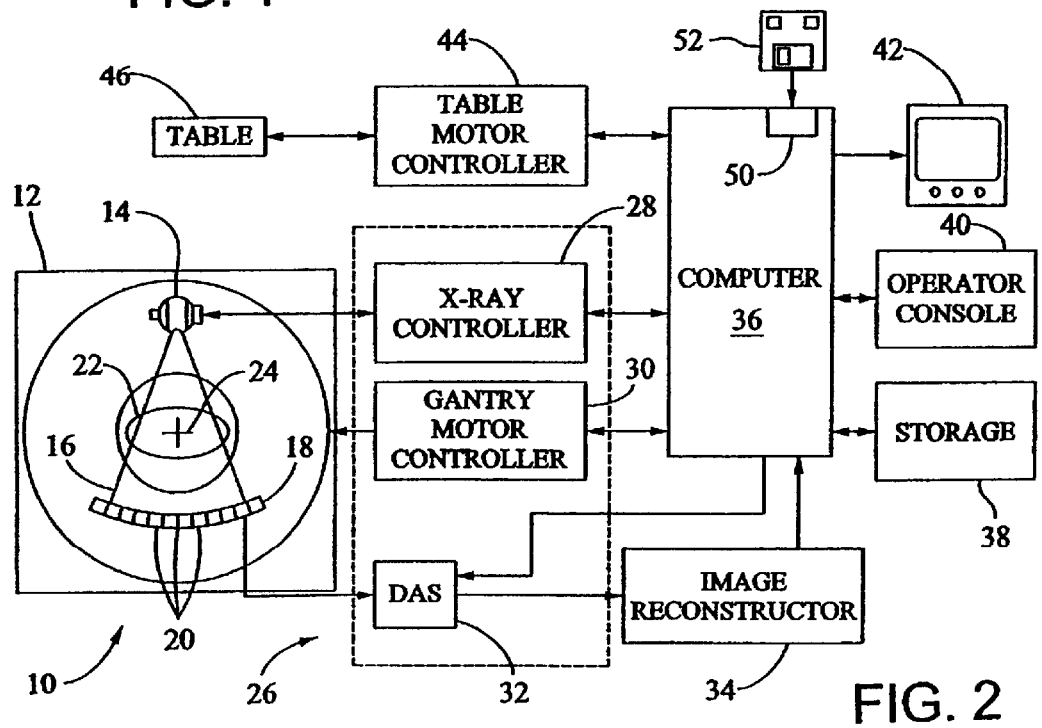
FIG. 2 is a block schematic diagram of the system illustrated in FIG. 1.

Referring to FIGS. 1 and 2, a computed tomography (CT) imaging system 10 is shown as including a gantry 12 representative of a "third generation" twin beam CT scanner. Gantry 12 has an x-ray radiation source 14 that projects a beam of x-ray radiation 16 toward a detector array 18 on the opposite side of gantry 12. Detector array 18 is formed by detector elements 20 that together sense the projected x-rays that pass through an object 22, for example a medical patient. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24. Detector array 18 is fabricated in a multi-slice configuration such that detector array 18 has a plurality of rows of detector elements or cells 20, only one of which is shown in FIG. 2. During a twin beam helical scan, data is acquired from two detector rows at the same time. One or more additional rows of detector elements 20 in such configurations are arranged parallel to the illustrated row, and each row is transverse to the translation direction of patient 22 (i.e., the z-axis or patient axis).

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements or cells 20 and converts the data to digital signals for subsequent processing. An image reconstructor 34 receives sampled and digitized x-ray data from DAS 32 and performs high-speed image reconstruction. The reconstructed image is applied as an input to a computer 36 which stores the image in a storage device 38. Computer 36 also receives commands and scanning parameters from an operator via console 40 that has a keyboard. An associated display 42, such as a cathode ray tube or a liquid crystal display, allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50 for reading and writing onto removable media 52. For example, device 50 is a floppy disk drive, a CD-R/W drive, or a DVD drive. Correspondingly, media 52 is either a floppy disk, a compact disk, or a DVD. Device 50 and media 52 are used in one embodiment to transfer acquired projection data from imaging system 10 to another computer for further processing, or in another embodiment to input machine readable instructions that are processed by computer 36.

Computer 36 and/or image reconstructor 34 of imaging system 10, either alone or in combination, provide the processing power necessary to perform the computational steps described herein in at least one embodiment of the present invention. Instructions for performing the computational steps are stored in an associated memory, such as storage device 38, read only or read/write memory (not shown separately in FIG. 1), or media 52. As used herein, the term computer is not limited to just those integrated circuits referred to in the art as computers, but broadly refers to computers, processors, microcontrollers, microcomputers, application specific integrated circuits, and other programmable circuits.

Figure 3:
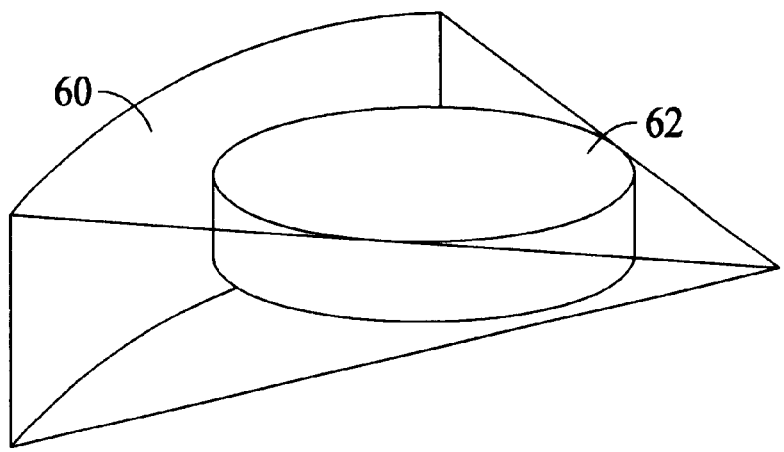
FIG. 3 is a three-dimensional illustration of a volume coverage area.
Figure 4:
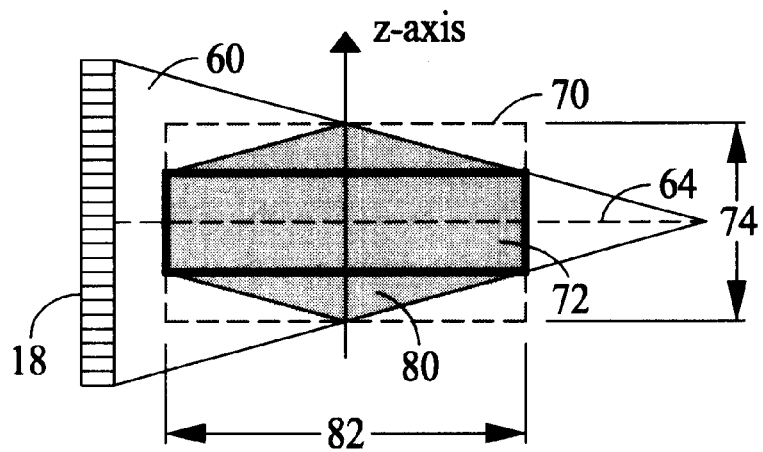
FIG. 4 is a cross-sectional view of a volume coverage area.

FIG. 3 is a three-dimensional illustration of a volume coverage area 60 of multi-slice CT imaging system 10 wherein a reconstructed volume 62 for an axial scan is depicted as a cylindrical shaped region 62. FIG. 4 is a cross-sectional view of volume coverage area 60 of CT imaging system 10 showing an iso-channel plane 64, i.e. a plane parallel to the z-axis, and passing through both an x-ray focal spot and at least two detector iso-channels. Referring to FIG. 4, volume of coverage 60 includes a desired reconstruction volume 70 and an actual reconstruction volume 72. A height 74 of desired reconstruction volume 70 is identical to a projected height of detector 18 at a detector iso-center. For example, for an eight-slice CT imaging system 10, height 74 of desired reconstruction volume 70 is 20 millimeters (mm), since the projected detector height at the iso-center is 20 mm. To facilitate an artifact-free reconstruction, every voxel in a reconstructed image should be sampled from all views. The volume that satisfies this condition is depicted by a volume 80. In order to obtain a continuous reconstruction volume with multiple axial scans, the reconstructed volume for each scan is limited to actual reconstruction volume 72 which is enclosed inside volume 80. As a result, the distance between the adjacent axial scans cannot be larger than a length 82 of actual reconstruction volume 72. If a projected detector width at the iso-center is denoted by D, a source-to-iso distance is denoted by S, and a radius of the reconstruction FOV (x-y) is denoted by R, a distance t, between adjacent axial scans for continuous coverage will satisfy the following condition:

$$t \leq \left(\frac{S-R}{S}\right)D \qquad \text{Equation 1}$$

For example, for CT system 10 with S=541 mm, R=250 mm, and D=20 mm, the actual reconstruction volume 72 that can be covered by each axial scan is 10.8 mm. To obtain a continuous coverage of an organ, the distance between adjacent scans is limited to 10.8 mm, which is approximately one-half of detector 18 z-coverage at the detector iso-channel. Therefore, volume coverage 60 of a scanner is significantly reduced.

Figure 5:
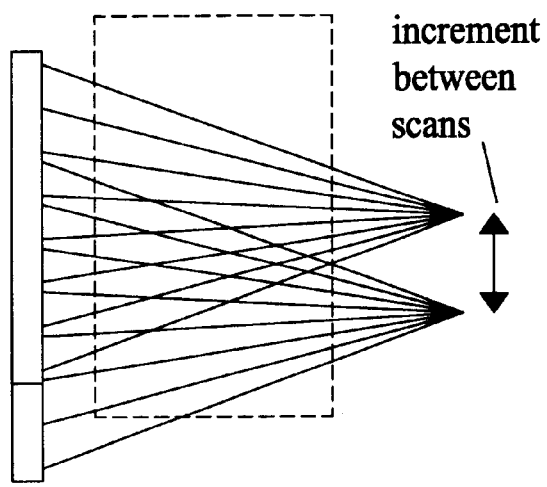
FIG. 5 is a cross-sectional view of a typical sampling pattern.

FIG. 5 is a sampling pattern of an 8-slice imaging system 10. To fulfill the continuous volume coverage requirement as described in the previous paragraph, an increment, a distance in z, between adjacent scans has to satisfy Equation 1. As shown in FIG. 5 it is not clear that any duplicated samples exist between the adjacent scans.

Figure 6:
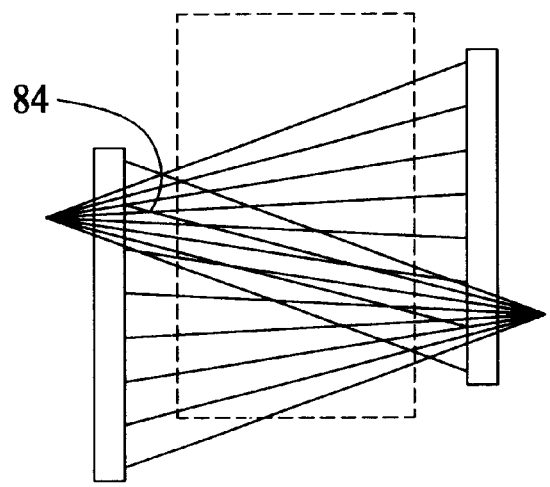
FIG. 6 is a cross-sectional view of a typical sampling pattern illustrating original and conjugate samples.

FIG. 6 is a cross-sectional view of a sampling pattern illustrating original and conjugate samples from adjacent scans. As shown in FIG. 6, a redundant sampling region 84 does not contribute new information to the formation of the images, other than reducing the noise in the samples. Therefore, adjacent axial scans can be placed further apart to avoid duplicated samples.

Figure 7:
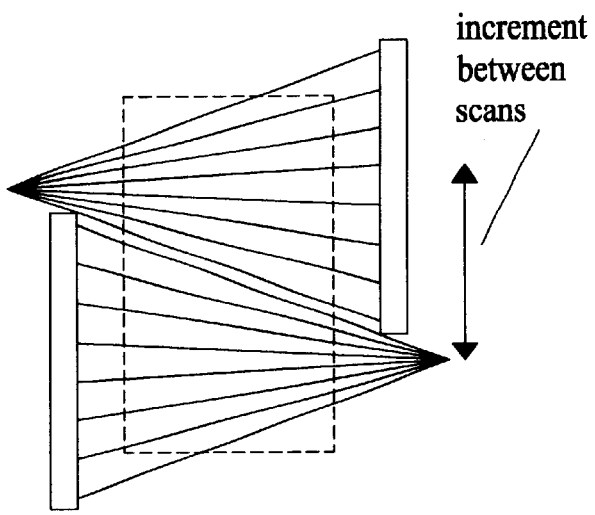
FIG. 7 is a cross-sectional view of a sampling pattern achieved using adjacent axial scans.

FIG. 7 is a cross-sectional view of a sampling pattern achieved using adjacent axial scans. In one embodiment, setting t =D satisfies the condition in which no duplicated samples from adjacent scans occur.

Figure 8:
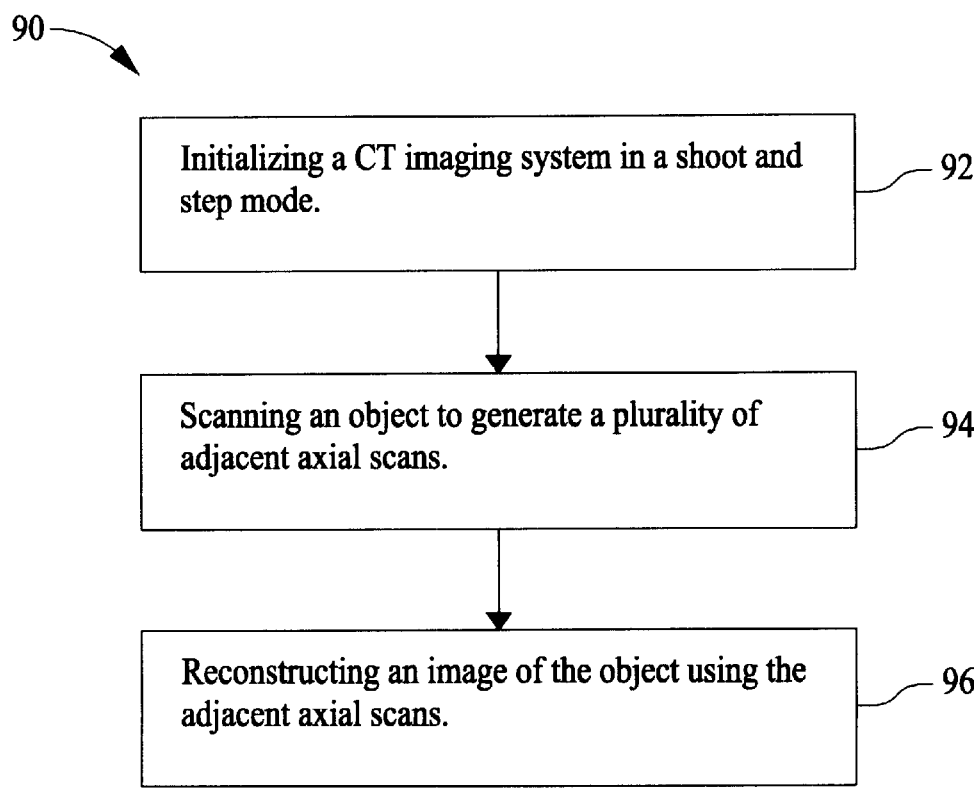
FIG. 8 is a flow diagram of a method for facilitating a reduction in reconstructed image noise.

FIG. 8 is a flow diagram of a method 90 for reconstructing a computed tomographic (CT) image of an object. Method 90 includes initializing 92 a CT imaging system 10 in a step-and-shoot mode, scanning 94 an object 22 to generate a plurality of adjacent axial scans, wherein the distance between the adjacent axial scans is approximately equal to a projected detector height at the detector iso-center, and reconstructing 96 an image of object 22 using the adjacent axial scans.

In one embodiment, the overall sampling pattern for adjacent scans is examined rather than examining the volume coverage individually. Therefore, a higher increment between the scans can be achieved by utilizing a plurality of overlapping samples from adjacent scans.

In another embodiment, the value of t can be selected approximately equal to and slightly smaller than D such that a relatively small overlapped region exists between the adjacent scans. For example, in one embodiment, t is selected to be 90 percent of D. Alternatively, t is selected to be less than 4 centimeters smaller than D. This region can be used to blend the two scans together to avoid any discontinuities. This is particularly important when a real patient is scanned, since the patient is likely to move between the scans.

Reconstructing 96 an image of object 22 using the adjacent axial scans includes rebinning the original cone beam projection samples to a set of tilted parallel geometry samples. Rebinning the original cone beam samples can be implemented in software by interpolation. In one embodiment, a reconstruction algorithm for tilted parallel geometry is:

$$f(x, y, z) = \int_0^{2\pi} \frac{d}{\sqrt{d^2 + Z^2}} \left[ \int_0^{\infty} S_\beta(\omega, Z) e^{j2\pi\omega t} \omega d\omega \right] d\beta \quad (3)$$

where $$S_\beta(\omega, Z) = \int_{-\infty}^{\infty} P_\beta(t, Z) e^{-j2\pi\omega t} dt$$

wherein $P_\beta(t, Z)$ is the projection intersecting point (x,y,z); and
$\beta$ is a projection angle.

Figure 9:
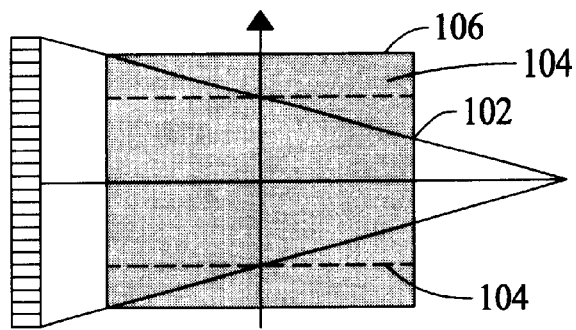
FIG. 9 is a cross-sectional view of a sampling pattern achieved using a single scan for some reconstruction planes.

FIG. 9 is a cross-sectional view of a sampling pattern achieved using a single scan for some reconstruction planes depicted in FIG. 9 as region 102. For other planes, the samples have to be collected from two adjacent scans (region 70 outside region 72). For image reconstruction, one can rearrange the collected projections samples from adjacent axial scans to formulate a single set of projections. Note that this "composite" projection has multiple "focal points" in z. Although the calculation for the backprojection is slightly more complicated, the weighting and filtering process remain the same.

Tilted parallel geometry facilitates simplifying the computations associated with the backprojection as compared to the cone beam process. Note that the distance squared weighting factor is not present in the backprojection. Because of the parallel nature of the projection samples, the calculation of the intersection with the neighboring projection rays can be a simple addition. Second, after the data is re-binned to parallel geometry, it is much easier to design different weighting schemes. For example, at the slice locations where two scans are needed to reconstruct an image, the two scan data can be blended more readily by projection weighting with parallel geometry.

Alternatively, images can be reconstructed using a cone beam reconstruction algorithm after weighting adjacent data sets to avoid duplicated samples. The weighting process can be achieved either in a projection space or in an image space.

In another embodiment, images are reconstructed based on each individual axial scans. Each filtered projection sets are artificially extended in z by padding zeroes. For example, an 8-row projection is extended to 16-rows by padding 4 rows of zeros on both ends (in z) of the 8-row projection. During reconstruction process, a volume 74 is reconstructed since the extended projection covers the volume at all time. Similarly, projections of the adjacent axial scans are extended and image volume is reconstructed. The image volumes from adjacent axial scans now represent partially overlapped volumes. At the overlapped regions, the two image sets can be weighted and summed (or simple summation).

Alternatively, one can perform backprojection process first with adjacent axial scans. A 2D or 3D filter is then applied to the backprojected volume to obtain the final image.

Figure 10:
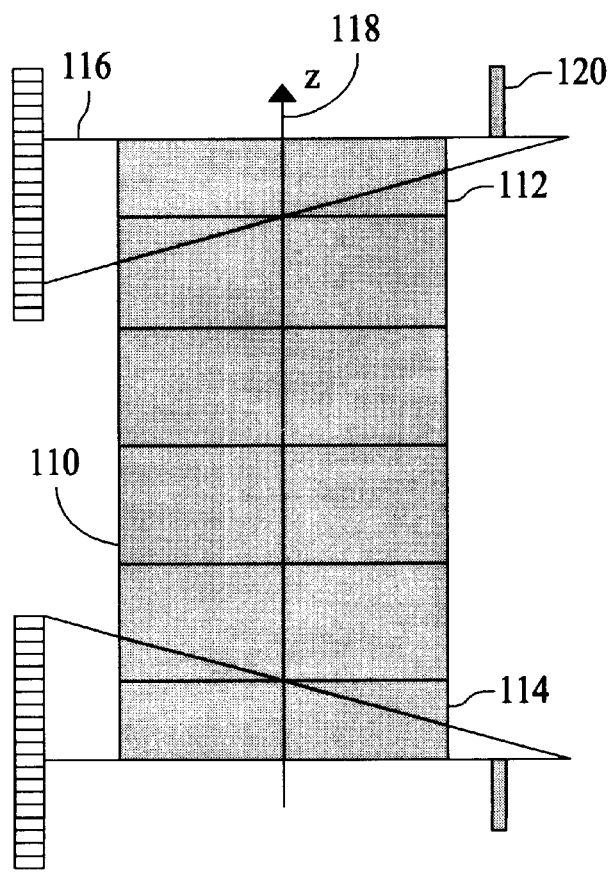
FIG. 10 is a cross-sectional view of a sampling pattern achieved using half-cone beam scanning.

For example and referring to FIG. 10, for an entire scanned volume 110 including a top sub-portion 112 and a bottom sub-portion 114, half-cone beam scans 112 are used on top and bottom sub-portions 112 and 114 of volume 110. Since a boundary scan plane 116 is perpendicular to a z-axis 118, a complete reconstruction can be performed at this plane without relying on an adjacent volume. Note that volumes 112 and 114 are roughly half of volume 70 in FIG. 4. To lower an x-ray dose to a patient, a collimator 120 is used to block the upper portion of the x-ray during the boundary axial scan. A similar configuration is also used for bottom portion 114 of volume 110, as shown in FIG. 10.

While the invention has been described in terms of various specific embodiments, those skilled in the art will recognize that the invention can be practiced with modification within the spirit and scope of the claims.

What is claimed is:

1. A method for reconstructing a computed tomographic (CT) image of an object, said method comprising:
   initializing a CT imaging system in a step-and-shoot mode;
   scanning an object to generate a plurality of adjacent axial scans, wherein the distance between the adjacent axial scans is approximately equal to a projected detector height at the detector iso-center; and reconstructing an image of the object using the adjacent axial scans.

2. A method in accordance with claim 1 further comprising rebinning the projection samples to a set of tilted parallel geometry samples.

3. A method in accordance with claim 1 further comprising reconstructing an image of the object using a tilted parallel beam reconstruction algorithm.

4. A method in accordance with claim 3 wherein the tilted parallel beam reconstruction algorithm is:

$$f(x, y, z) = \int_0^{2\pi} \frac{d}{\sqrt{d^2 + Z^2}} \left[ \int_0^{\infty} S_\beta(\omega, Z) e^{j2\pi\omega t} \omega d\omega \right] d\beta$$

where $$S_\beta(\omega, Z) = \int_{-\infty}^{\infty} P_\beta(t, Z) e^{-j2\pi\omega t} dt;$$

and wherein $P_\beta(t, Z)$ is a projection intersecting a point (x,y,z); and $\beta$ is a projection angle.

5. A method for reconstructing a computed tomographic (CT) image of an object, said method comprising:
    initializing a CT imaging system in a step-and-shoot mode;
    performing at least one axial scan to generate a plurality of projection samples;
    rebinning the projection samples to a set of tilted parallel geometry samples; and
    reconstructing an image of the object using the rebinned projection samples.

6. A method in accordance with claim 5 further comprising reconstructing an image of the object using a tilted parallel beam reconstruction algorithm.

7. A method in accordance with claim 6 wherein the tilted parallel beam reconstruction algorithm is:

$$f(x, y, z) = \int_0^{2\pi} \frac{d}{\sqrt{d^2 + Z^2}} \left[ \int_0^{\infty} S_\beta(\omega, Z) e^{j2\pi\omega t} \omega d\omega \right] d\beta$$

where $$S_\beta(\omega, Z) = \int_{-\infty}^{\infty} P_\beta(t, Z) e^{-j2\pi\omega t} dt;$$

and wherein $P_\beta(t, Z)$ is a projection intersecting a point (x,y,z); and $\beta$ is a projection angle.

8. A method in accordance with claim 1 wherein said reconstructing an image of the object using the adjacent axial scans comprises rearranging multiple axial projections into a single projection with multiple focal points.

9. A method in accordance with claim 1 wherein said reconstructing an image of the object using the adjacent axial scans comprises extending a plurality of projections and reconstructing a larger volume for a later blending operation.

10. A method in accordance with claim 1 wherein said reconstructing an image of the object using the adjacent axial scans comprises reconstructing images with a cone beam reconstruction algorithm.

11. A method in accordance with claim 1 wherein said reconstructing an image of the object using the adjacent axial scans comprises reconstructing images with a cone beam reconstruction algorithm after weighting adjacent data sets to avoid duplicated samples.

12. A method in accordance with claim 1 further comprising:
    backprojecting the adjacent axial scans; and
    filtering the backprojected scans.

13. A method in accordance with claim 1 wherein said reconstructing an image of the object using the adjacent axial scans comprises reconstructing images using a boundary scan plane perpendicular to a z-axis.

14. A method in accordance with claim 13 further comprising positioning a collimator approximately adjacent the boundary scan plane to reduce an x-ray dose to the object.

15. A computed tomographic (CT) imaging system for reconstructing an image of an object, said imaging system comprising:
    a detector array;
    at least one radiation source; and
    a computer coupled to said detector array and said radiation source,
    said computer configured to:
        initialize a CT imaging system in a step-and-shoot mode;
        scan an object to generate a plurality of adjacent axial scans, wherein the distance between the adjacent axial scans is approximately equal to a projected detector height at the detector iso-center; and
        reconstruct an image of the object using the adjacent axial scans.

16. A CT imaging system in accordance with claim 15, wherein said computer is further configured to rebin the projection samples to a set of tilted parallel geometry samples.

17. A CT imaging system in accordance with claim 15, wherein said computer is further configured to reconstruct an image of the object using a tilted parallel beam reconstruction algorithm.

18. A CT imaging system in accordance with claim 17, wherein to reconstruct an image of the object using a tilted parallel beam reconstruction algorithm, said computer further configured to reconstruct an image of the object in accordance with:

$$f(x, y, z) = \int_0^{2\pi} \frac{d}{\sqrt{d^2 + Z^2}} \left[ \int_0^{\infty} S_\beta(\omega, Z) e^{j2\pi\omega t} \omega d\omega \right] d\beta$$

where $$S_\beta(\omega, Z) = \int_{-\infty}^{\infty} P_\beta(t, Z) e^{-j2\pi\omega t} dt;$$

and wherein $P_\beta(t, Z)$ is a projection intersecting a point (x,y,z); and $\beta$ is a projection angle.

19. A CT imaging system in accordance with claim 15, wherein said computer is further configured to rearrange multiple axial projections into a single projection with multiple focal points.

20. A CT imaging system in accordance with claim 15, wherein said computer is further configured to extend a plurality of projections and reconstructing a larger volume for a later blending operation.

21. A CT imaging system in accordance with claim 15, wherein said computer is further configured to reconstructing images with a cone beam reconstruction algorithm.

22. A CT imaging system in accordance with claim 15, wherein said computer is further configured to reconstructing images with a cone beam reconstruction algorithm after weighting adjacent data sets to avoid duplicated samples.

23. A CT imaging system in accordance with claim 15, wherein said computer is further configured to:
   backproject the adjacent axial scans; and
   filter the backprojected scans.

24. A CT imaging system in accordance with claim 15, wherein said computer is further configured to reconstruct an image using a boundary scan plane perpendicular to a z-axis.

25. A CT imaging system in accordance with claim 24, wherein said computer is further configured to position a collimator approximately adjacent the boundary scan plane to reduce an x-ray dose to the object.

26. A computer readable medium encoded with a program executable by a computer for reconstructing an image of an object, said program configured to instruct the computer to:
   initialize a CT imaging system in a step-and-shoot mode;
   scan an object to generate a plurality of adjacent axial scans, wherein the distance between the adjacent axial scans is approximately equal to a projected detector height at the detector iso-center; and
   reconstruct an image of the object using the adjacent axial scans.

27. A computer readable medium in accordance with claim 26, wherein said program is further configured to instruct the computer to rebin the projection samples to a set of tilted parallel geometry samples.

28. A computer readable medium in accordance with claim 26, wherein said program is further configured to instruct the computer to reconstruct an image of the object using a tilted parallel beam reconstruction algorithm.

29. A computer readable medium in accordance with claim 28, wherein to reconstruct an image of the object using a tilted parallel beam reconstruction algorithm, said program is further configured to reconstruct an image of the object in accordance with:

$$f(x, y, z) = \int_0^{2\pi} \frac{d}{\sqrt{d^2 + Z^2}} \left[ \int_0^{\infty} S_\beta(\omega, Z) e^{j2\pi\omega t} \omega d\omega \right] d\beta$$

where $$S_\beta(\omega, Z) = \int_{-\infty}^{\infty} P_\beta(t, Z) e^{-j2\pi\omega t} dt;$$

and wherein $P_\beta(t, Z)$ is a projection intersecting point a (x,y,z); and $\beta$ is a projection angle.

* * * * *